United States Patent [19]

Goudie et al.

[11] 4,359,423

[45] Nov. 16, 1982

[54] 10H-1-ALKYL-10-OXABENZO,5,6 CYCLOHEPTA[1,2-G]PYRROLE-2-ACETIC ACIDS

[75] Inventors: Alexander C. Goudie; Robert W. Ward, both of Harlow, England

[73] Assignee: Beecham Group Limited, England

[21] Appl. No.: 172,419

[22] Filed: Jul. 25, 1980

[51] Int. Cl.³ .................... C07D 209/52; A61K 31/40
[52] U.S. Cl. ..................................... 548/427; 424/274
[58] Field of Search .................. 260/326.27, 326.5 B

[56] References Cited

U.S. PATENT DOCUMENTS

| | | | |
|---|---|---|---|
| 3,202,676 | 8/1965 | Rice et al. | 260/326.5 B |
| 3,397,202 | 8/1968 | Plostnicks | 260/326.27 |
| 4,075,225 | 2/1978 | Rokach et al. | 260/326.5 B |

FOREIGN PATENT DOCUMENTS 44-15648  7/1969  Japan ........................... 260/326.5 B

*Primary Examiner*—David B. Springer

*Attorney, Agent, or Firm*—Jacobs & Jacobs

[57] ABSTRACT

A compound of formula (II):

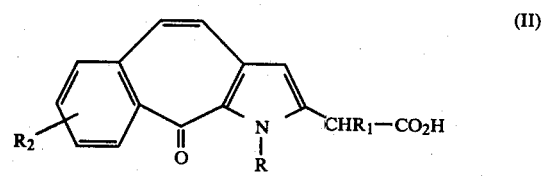

(II)

wherein
R is a $C_{1-4}$ alkyl group;
$R_1$ is a hydrogen atom or a $C_{1-4}$ alkyl group;
$R_2$ is a hydrogen or halogen atom, or a $C_{1-4}$ alkyl, $C_{1-4}$ alkoxy or $C_{1-4}$ alkylthio group;

and pro-drugs thereof; and the pharmaceutically acceptable salts of the compounds of formula (II) and of their pro-drugs; has useful anti-inflammatory and analgesic activity.

5 Claims, No Drawings

10H-1-ALKYL-10-OXABENZO,5,6 CYCLOHEPTA[1,2-G]PYRROLE-2-ACETIC ACIDS

This invention relates to novel compounds having anti-inflammatory and analgesic activity, to a process for their preparation, and to pharmaceutical compositions containing them.

Tolmetin, a clinically used anti-inflammatory and analgesic agent of the formula (I):

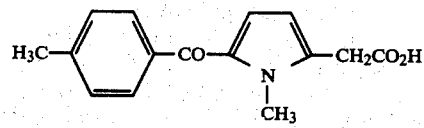

and related compounds have been described in J Pharmacol Exp Therap 1973, 185, 127–138, US Patent Specification No. 3 752 826 and UK Patent Specification No. 1 195 628.

It has now been found that certain other structurally distinct acetic acid derivatives possess good anti-inflammatory and analgesic activity without undue gastric side effects. Accordingly, the present invention provides the compounds of the formula (II):

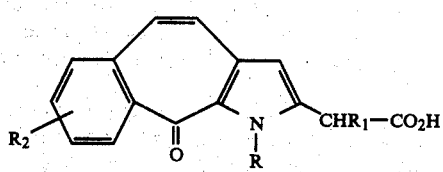

wherein
R is a $C_{1-4}$ alkyl group;
$R_1$ is a hydrogen atom or a $C_{1-4}$ alkyl group;
$R_2$ is a hydrogen or halogen atom, or a $C_{1-4}$ alkyl, $C_{1-4}$ alkoxy or $C_{1-4}$ alkylthio group;
and pro-drugs thereof; and the pharmaceutically acceptable salts of the compounds of formula (II) and of their pro-drugs.

Suitable examples of R include methyl and ethyl. Preferably R is methyl.

Suitable examples of $R_1$ include hydrogen, methyl and ethyl. More suitable $R_1$ is hydrogen. $R_1$ may also with advantage be methyl.

Suitable examples of $R_2$ include hydrogen; fluorine, chlorine, bromine; methyl, ethyl, propyl; methoxy; and methylthio. The position of substitution for $R_2$ is suitably the 6, 7 or 8 position, more suitably the 7 or 8 position. A preferred position of substitution for $R_2$, if present, is the 7 position. Most suitably $R_2$ is methyl or chlorine. Preferably $R_2$ is hydrogen.

A second sub-group within formula (II) is of formula (III):

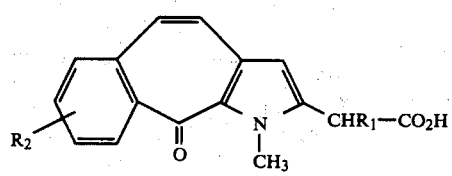

wherein $R_1$ is a hydrogen atom or methyl group and $R_2$ is a hydrogen, fluorine, chlorine or bromine atom or a methyl, ethyl, propyl, methoxy or methylthio group; and pharmaceutically acceptable salts and pro-drugs thereof.

Within this sub-group of formula (III) there is a preferred sub-group of formula (IV):

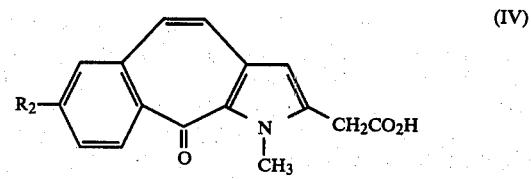

wherein $R_2$ is as defined in formula (III), and pharmaceutically acceptable salts and pro-drugs thereof.

Within formulae (III) and (IV) suitable and preferred examples of the variables are as described hereinbefore in regard to formula (II).

Particularly suitable pharmaceutically acceptable salts for this invention include alkali metal and alkaline earth metal salts such as the sodium, potassium, calcium and magnesium salts and salts of pharmaceutically acceptable nitrogenous bases such as the ammonium salt.

When used herein the term "pro-drug" means a compound metabolised in vivo to a compound of the formula (II) or its salt. A pro-drug may be identified by administering the pro-drug to a mammal such as a rat, mouse, monkey or man and identifying the compound of the formula (II) or its salt, for example in blood or urine.

When used herein the term "lower" means containing 1, 2, 3 or 4 carbon atoms. A particularly suitable lower alkyl group is the methyl group.

One class of pro-drugs of the compounds of the formula (II) are in vivo hydrolysable esters. Such esters may be simply substituted alkyl esters such as the methoxymethyl, 2-methoxyethyl, 2-hydroxyethyl, 2-dimethylaminoethyl, or benzyl esters of other esters conventionally used in the medical arts as pro-drugs such as a lower acyloxymethyl, α-lower acyloxyethyl, lower alkoxycarbonyloxymethyl, α-lower alkoxycarbonyloxymetyl, phthalidyl or like ester.

A further class of pro-drugs for the compounds of the formula (II) are in vivo hydrolysable amides thereof such as the primary amide, lower alkylamides and di-lower alkylamides thereof.

Another class of pro-drugs for the compounds of the formula (II) are the analogous compounds of lower oxidation state, namely the corresponding compounds in which the $CO_2H$ group is replaced by a CHO or $CH_2OH$ group.

A particularly suitable class of pro-drugs are those wherein the $CO_2H$ group of the compound of the formula (II) [or (III), and (IV)] is replaced by a group of the sub-formulae (a)–(j):

| | |
|---|---|
| -CH$_2$-CO-CH$_3$ | (a) |
| -CH$_2$-CHOH-CH$_3$ | (b) |
| -CHOH-CHOH-CH$_3$ | (c) |
| -CHOH-CO-CH$_3$ | (d) |
| -CH$_2$-CH(OCOR$_3$)-CH$_3$ | (e) |
| -CH=C(OR$_4$)-CH$_3$ | (f) |
| -CH$_2$-C(OR$_4$)=CH$_2$ | (g) |

-CH$_2$-C(OR$_5$)OR$_6$-CH$_3$     (h)

-CH$_2$-C(OCOR$_7$)=CH$_2$     (i)

-CH=C(OCOR$_7$)-CH$_3$     (j)

In these sub-formulae R$_3$ is a phenyl or substituted phenyl group or a C$_{1-4}$ alkyl group optionally substituted by a phenyl or amino group (for example methyl and aminomethyl); R$_4$ is a lower alkyl group; R$_5$ and R$_6$ are each lower alkyl groups or are joined to represent a CH$_2$CH$_2$ or CH$_2$CH$_2$CH$_2$ group; and R$_7$ is a lower alkyl group.

Preferred pro-drugs are those containing subformulae (a), (b), (c), (d) and (e) as defined above. Particularly preferred pro-drugs are those containing sub-formulae (a) and (e).

The compounds of this invention are most suitably provided in crystalline form.

In a further aspect this invention provides a pharmaceutical composition which comprises a compound of the formula (II) and a pharmaceutically acceptable carrier.

The compositions of this invention are useful in treating rheumatic and arthritic conditions because of their anti-inflammatory and analgesic properties. The compositions may be adapted for administration via the oral, rectal or injection routes but since the compositions of this invention do not excessively irritate the gastro-intestinal tract it is preferred that they are adapted for oral administration.

The compositions of this invention may contain diluents, binders, fillers, disintegrants, flavouring agents, colouring agents, lubricants, preservatives or the like in conventional manner. These conventional excipients may be employed in conventional manner, for example as in the preparation of compositions of ketoprofen, indomethacin, naproxen, acetylsalicyclic acid or other anti-inflammatory analgesic agents.

Most suitably the composition of this invention will be in the form of a unit dose such as a tablet, capsule or reconstitutable powder in a sachet. Such unit doses will generally contain from 20 mg to 1,000 mg and more suitably will contain from about 30 mg to 500 mg, for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range of 200 to 3,000 mg and more usually in the range of 300 to 3,000 mg for example 500 to 2,000 mg. Alternatively the unit dose may contain from 2 to 20 mg of active agent and may be administered in multiples if desired to give the preceeding daily dose.

A favoured form of the composition of this invention is a hard gelatin capsule containing the active agent. The active agent may be in the form of a powder, granulate or the like and may advantageously be in intimate mixture with a lubricant such as magnesium stearate.

A further favoured form of the composition of this invention is a tablet containing the active agent The active agent may be in the form of a recompressed granulate of the active ingredient in intimate mixture with a lubricant such as magnesium stearate, a filler such as microcrystalline cellulose and disintegrant such as sodium starch glycollate.

This present invention also provides a method of treating inflammatory and/or painful conditions in mammals which comprises administering per day an effective amount, such as from 50 to 4,000 mg, of a compound of this invention and more usually from 100 to 3,000 mg for example from 100 to 1,500 of a compound of this invention.

Mammals which may be thus treated include humans and domestic animals such as dogs, cats or horses.

Most suitably the medicament will be administered orally as 2, 3 or 4 doses per day at the dose level previously indicated.

The invention also provides a process for the preparation of a compound of the formula (II), its pharmaceutically acceptable salts and pro-drugs, For easy reference, the following Scheme shows a synthetic pathway leading to the compounds of the formula (II);

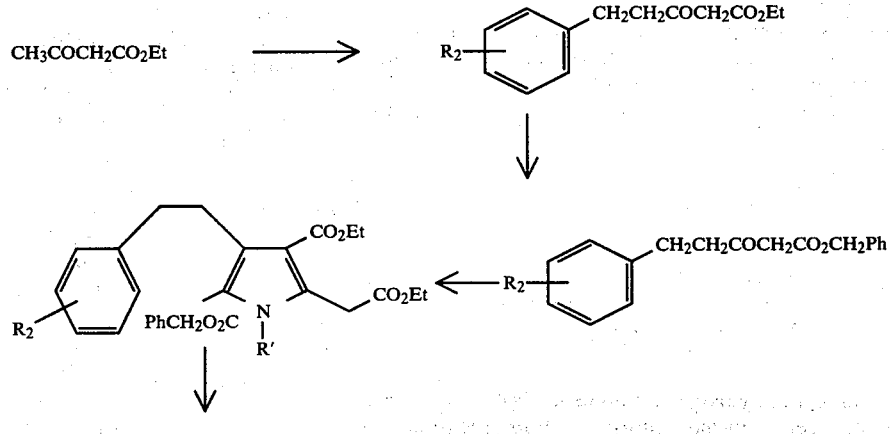

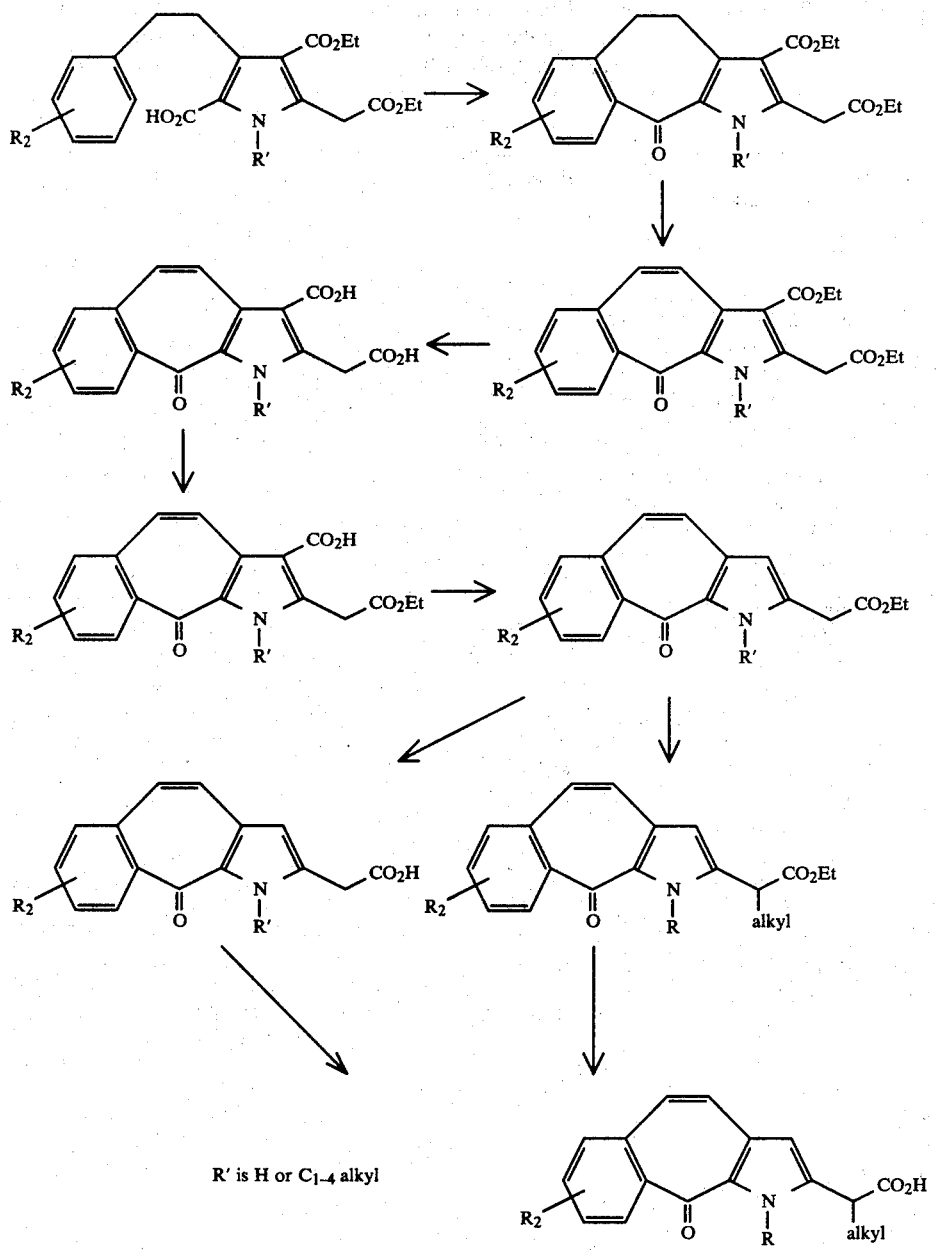

R' is H or $C_{1-4}$ alkyl

From the foregoing reaction Scheme it can be seen that the present invention provides a preferred process for the preparation of a compound of the formula (II) which comprises the basic hydrolysis of an ester of the formula (V):

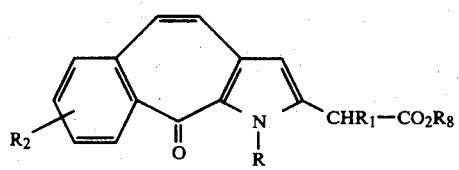

(V)

wherein $R_8$ is $C_{1-4}$ alkyl, such as ethyl, and the other variables are as defined in relation of formula (II); and thereafter if desired acidifying the resulting salt to form the free acid; and alkylating a compound in which $R_1$ is hydrogen to give the corresponding compound in which $R_1$ is alkyl.

The hydrolysis may be effected by using an hydroxide such as sodium hydroxide in aqueous ethanol.

The conversion of the thus formed salt to the free acid may be effected in conventional manner with an acid, such as hydrochloric acid.

The optional alkylation to convert a $R_1$ is hydrogen compound of formula (II) to a $R_1$ is $C_{1-4}$ alkyl compound of formula (II) can be carried out in conventional manner, for example with lithium diisopropylamide and an alkyl halide such as methyl iodide.

The compounds of formula (V) wherein $R_1$ is alkyl may be prepared from the corresponding compounds of the formula (V) wherein $R_1$ is hydrogen, by alkylation. This alkylation may conveniently be carried out using sodium hydride and an alkyl halide such as methyl iodide.

Alternatively, in a further process of the invention for the preparation of compounds of the formula (II), a compound of formula (VI):

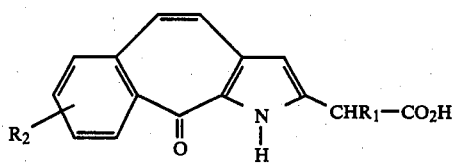
(VI)

is alkylated; and thereafter if desired a salt thereof is formed; or a compound of the formula (II) in which $R_1$ is hydrogen is alkylated to give the corresponding compound wherein $R_1$ is alkyl.

The alkylation of the compound of formula (VI) is suitably carried out using lithium diispropylamide and dimethylsulphate.

If this alkylation reaction is on a compound of formula (VI) wherein $R_1$ is hydrogen, and is carefully controlled then a compound of formula (II) wherein $R_1$ is hydrogen will result. In such cases if desired the further conversion of the $R_1$ group to alkyl may be carried out by further reaction under similar conditions.

The compound of formula (VI) may be prepared from a compound of formula (V)':

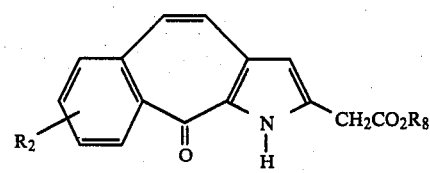
(V)' by basic hydrolysis as described in relation to formula (V).

The intermediates of formula (V)', and the intermediates of formula (V), may be written with structure (V)'':

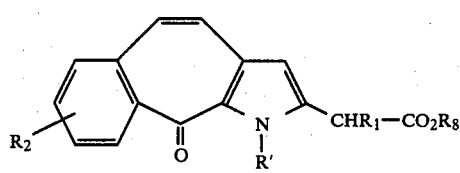
(V)'' wherein R' is hydrogen or $C_{1-4}$ alkyl; and may themselves be prepared by decarboxylation of a compound of formula (VII):

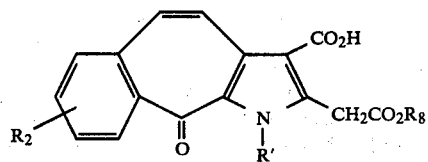
(VII)

; and subsequent optional alkylation of a $R_1$ is hydrogen compound of formula (V)'' to give a compound of the formula (V)'' wherein $R_1$ is alkyl. This decarboxylation may best be achieved by heating in an inert atmosphere, at a temperature such as 170°–240° C. Alternatively a high boiling point solvent such as diethyl formamide, ethanolamine or quinoline (with or without copper) may be used in the reaction. When R' is alkyl in the thus formed compound of formula (V)'', then the optional $R_1$ alkylation can be carried out using sodium hydride and an alkyl halide. When R' is hydrogen in the thus formed compound, then the optional $R_1$ alkylation can be carried out using $K_2CO_3$ and an alkyl halide.

Compounds of formula (VII) may be prepared by the de-esterification of a compound of formula (VIII):

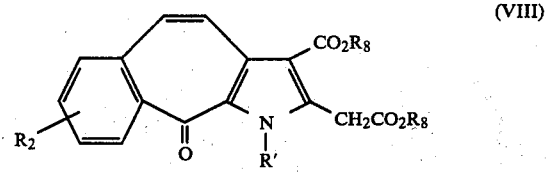
(VIII)

, and then subsequent selective esterification of the acetic acid function.

These reactions may be carried out in conventional manner, for example as illustrated in the specific Descriptions.

Compounds of the formula (VIII) may be prepared from the corresponding compound of the formula (VIII) wherein the double bond is not present, by oxidation. Suitably this reaction may be carried out with N-bromosuccinimide, and depending on the reaction conditions may go directly to the desired double bond compound, or may form an intermediate dibromo derivative

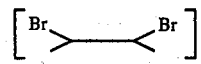

which is convertable to the desired end product with zinc and methanol.

Compounds of formula (VIII) (wherein the optional double bond is not present) may be prepared by the cyclisation of a compound of formula (IX):

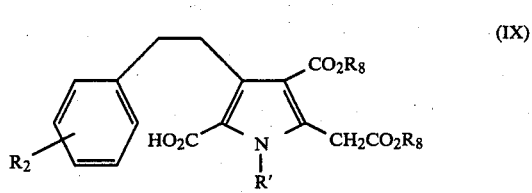
(IX)

, followed by optional alkylation of a thus formed compound of formula (VIII) wherein R' is hydrogen (with for example $K_2CO_3$ and dimethylsulphate). This cyclisation reaction is suitably carried out with a strong acid, such as polyphosphoric acid or methane sulphonic acid/$P_2O_5$. When R' is alkyl, the cyclisation may also be carried out by a Friedel-Crafts reaction, using a Lewis acid such as $AlCl_3$ or $SnCl_4$ and the acid of formula (IX) in the form of its acid chloride or mixed anhydride.

Compounds of the formula (IX) may themselves be prepared by reacting a compound of formula (X):

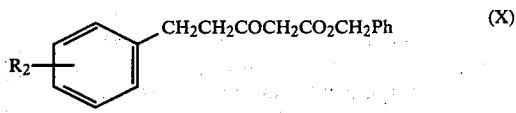
(X)

in a Knorr synthesis; and subsequently, if necessary, alkylating the pyrrole N-hydrogen; and then converting the benzyl ester to the free acid.

The Knorr pyrrole synthesis is suitably carried out with sodium nitrite, diethyl acetone-1,3-dicarboxylate and zinc, in acetic acid.

The N-H alkylation may suitably be carried out with K₂CO₃ and a dialkyl sulphate such as dimethyl sulphate.

The description above describes suitable processes for preparing the compounds of formula (II). There are however a number of process variations which should be noted.

(i) Instead of the compound of formula (X) the corresponding dialkylamide or morpholide may be used, in which case suitably POCl₃ may be used in the subsequent cyclisation reaction, with or without a solvent.

(ii) Any readily hydrolysable or hydrogenolysable ester may be used in the place of the benzyl ester in the compound of formula (X). For example the t-butyl ester may be used, and after the Knorr pyrrole synthesis hydrolysis thereof is simply achieved with dilute hydrochloric acid.

(iii) R₂ groups may be interchanged at suitable points in the synthetic sequence. For example when R₂ is 7-fluoro compounds of the formula (VIII) may be converted to the corresponding R₂ is alkoxy or alkyl thio compounds by reaction with a source of alkoxide or alkylthio ion.

(iv) The cyclisation reaction may be carried out exactly as described above, but on a compound of the formula (IX)':

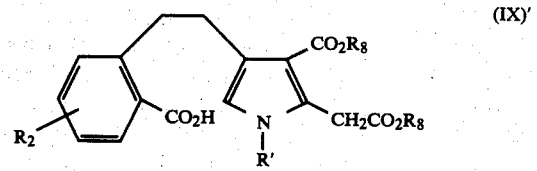

This compound of formula (IX)' may be derived from the corresponding compound of formula (IX) by thermal decarboxylation. Otherwise the compound of formula (IX)' may be prepared in analogous manner to the compounds of formula (IX) but using a readily hydrolysable or hydrogenolysable (eg benzyl) ester of a compound of formula (X)':

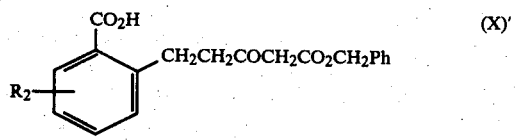

It will be appreciated that in this alternative cyclisation scheme variations (i) and (ii) above may be incorporated if desired.

The salts of the compounds of formula (II) may be prepared from the free acids of the formula (II) in any of the conventional ways used to convert an acid to its salt.

The pro-drugs of the compounds of the formula (II) may either be prepared from the compounds of formula (II), or may be synthesised "independently", as appropriate.

All such processes of course form part of this invention.

Examples of preparation of pro-drugs from compounds of the formula (II) include esterification and amidation.

Examples of "independent" synthesis include the preparation of a compound of the formula (II) wherein the CO₂H group is replaced by a CH₂COCH₃ group (ie sub-formula (a)), by the oxidation of a compound of the formula (XI):

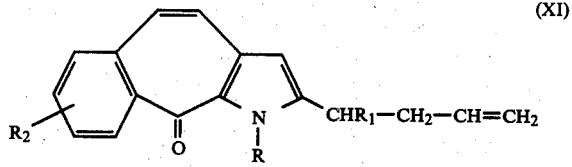

This oxidation may be carried out in any convenient manner for example with oxygen in aqueous dimethylformamide in the presence of palladium chloride and cuprous chloride. This oxidation reaction may be effected using pure oxygen or air. In general it is sufficient to blow air through the reaction mixture at an ambient or slightly elevated temperature to effect oxidation. The desired compound may be obtained from the reaction mixture by dilution with water followed by extraction into water-immiscible solvent such as chloroform which may then be dried and evaporated. This initial crude material may be purified chromatographically if desired, for example by column chromatography over silica gel using 1:1 ether: petrol eluant.

The compounds of the formula (XI) may be prepared by the decarboxylation of a corresponding compound of the formula (XII):

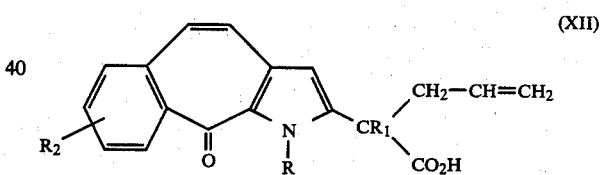

The decarboxylation may be effected by heating, for example to 170°–210° C. The desired product may be obtained by trituration using a non-hydroxylic solvent such as chloroform.

The acid of the formula (XII) may be obtained by hydrolysis of the corresponding C₁₋₄ alkyl ester such as the ethyl ester using normal sodium hydroxide solution followed by neutralisation with hydrochloric acid. This C₁₋₄ alkyl ester may be prepared by the allylation of the corresponding compound of the formula (V). Such allylations may be brought about by generating an anion of the formula (V) for example with sodium hydride in dimethoxyethane, and quenching said anion with allyl bromide.

Alternatively, compounds of the formula (XII) may be prepared by the direct allylation of a compound of formula (II) with for example allyl bromide in the presence of lithium diisopropylamide.

The pro-drugs of compounds of the formula (II) wherein the CO₂H group is replaced by a CH₂COCH₃ group may also be prepared by thermal decomposition of a compound of formula (XIII):

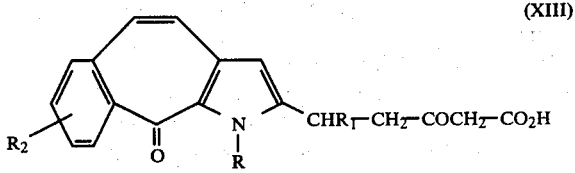

(XIII)

This decomposition may suitably be carried out with or without an inert solvent, such as dimethyl sulphoxide, at about 60° to 100° C.

The intermediates of formula (XIII) may themselves be prepared from a compound of formula (XIV):

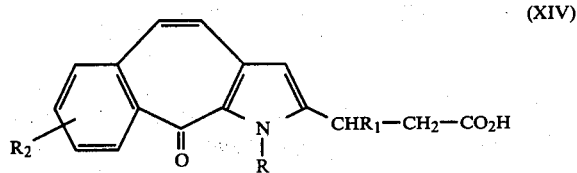

(XIV)

via a suitably activated derivatives such as the ethoxycarbonyl derivative, for example following the general method described in Synthesis 1979, p. 787.

It will be appreciated that the compounds of formula (XIV) may be prepared in analogous manner to the preparation of the corresponding compounds of formula (II) except that dimethyl 3-oxoadipate is suitably used in the Knorr pyrrole synthesis reaction.

Compounds of the formula (II) wherein the $CO_2H$ group is replaced by a group of the sub-formula (b) may be prepared by the reduction of a corresponding compound of the formula (II) wherein the $CO_2H$ group is replaced by a group of the sub-formula (a). Such a reduction may use a complex hydride such as sodium borohydride. Mild conditions and avoidance of excess reagent prevent reduction of the aromatic carbonyl. The desired compound may be purified by conventional methods of column chromatography.

Pro-drugs of the compounds of the formula (II) containing a group of the sub-formulae (e), (f), (g), (h), (i) and (j) may be prepared, for example as described in Belgian Pat. No. 866 857 (or Offenlegungsschrift No. P 28 19 463.0).

Thus compounds of the formula (II) wherein the $CO_2H$ group is replaced by the sub-formula (e) may be prepared by the acylation of a corresponding compound containing the sub-formula (b). Suitable methods of acylation include those described in Belgian Pat. No. 854 429 (or Offenlegungsschrift No. P 28 19 463.0).

Compounds of the formula (II) wherein the $CO_2H$ group is replaced by sub-formula (f) or (j); (g) or (i); or (h); may be prepared by the enol acylation or enol etherification of a corresponding compound containing the sub-formula (a). Suitable methods of enol acylation or enol etherification include those described in Offenlegungsschrift No P 26 47 966.3.

Also, compounds of the formula (II) wherein the $CO_2H$ group is replaced by a group of the sub-formula (d) may be prepared by the reaction of m-chloroperbenzoic acid and a compound of the formula (II) in which the $CO_2H$ group is replaced by a group of the sub-formula (f). Such reactions are generally carried out at 0°–5° C. in mixed solvents such as diethyl ether/water.

Compounds of the formula (II) wherein the $CO_2H$ group is replaced by a group of the sub-formula (c) may be prepared by reduction of a corresponding compound of the formula (II) in which the $CO_2H$ group is replaced by a group of the sub-formula (d). Such a reaction may be effected using sodium borohydride under conventional conditions.

As stated hereinbefore, other pro-drugs of the compound of formula (II) include the corresponding aldehyde and alcohol. The aldehyde may be prepared from the acid by reduction, for example via the acid halide (suitably chloride) in a Rosemund reduction. The alcohol may be prepared by reduction of the aldehyde, for example with sodium borohydride.

It will be appreciated that in the same way that, as hereinbefore described, the preparation of compounds of the formula (II) may entail as a last stage the alkylation of a N-hydrogen atom on the pyrrole moiety, the same can be true for the aforedescribed pro-drugs. Of course the N-H pro-drug intermediates for such a last stage alkylation can be prepared in analogous process to the corresponding N-alkyl pro-drugs.

The intermediates of formulae (V)", (VI), (VII), (VIII), (XI), (XII), (XIII) and (XIV) form an important part of this invention.

The following Descriptions illustrate the preparation of intermediates. The following Examples illustrate the preparation of the compounds of this invention.

DESCRIPTION 1(a)

Ethyl 3-oxo-5-phenylpentanoate

Ethyl acetoacetate (100 ml, 0.79 mole) in dry tetrahydrofuran (400 ml) was added dropwise with stirring under nitrogen to 50% sodium hydride (41.8 g, 0.87 mole) in dry tetrahydrofuran (80 ml) at 0° C. The resulting solution was stirred for 15 minutes at 0° C. before adding dropwise a solution of n-butyllithium in hexane (460 ml, 1.95 M; 0.90 mole). The resulting orange solution was stirred for a further 15 minutes at 0° C. before adding benzyl chloride (135 ml, 1.18 mole) in dry ether (200 ml) and the solution was then allowed to warm to room temperature over 1¼ hours with stirring before quenching reaction by addition of conc HCl acid (100 ml) in water (200 ml) followed by ether (500 ml). The layers were separated and the aqueous further extracted with ether (3×300 ml). The combined organic layers were washed with water until the wash was neutral, dried (anhydrous $MgSO_4$) and then concentrated. The resulting yellow oil was distilled under vacuum to give a virtually colourless oil (64.2 g, 37%), b.p. 118°–126° C. at 0.7 mmHg, n.m.r. δ ($CDCl_3$) 7.08 (5H, s), 4.07 (2H, q, J=7 Hz), 3.23 (2H, s), 2.80 (4H, s) and 1.23 (3H, t, J=7 Hz).

DESCRIPTION 1(b)

Benzyl 3-oxo-5-phenylpentanoate

Ethyl 3-oxo-5-phenylpentanoate (64.2 g, 0.29 mole) was heated between 190° and 210° C. under nitrogen with benzyl alcohol (28.9 ml, 0.28 mole) for 6 hours, the ethanol formed being distilled out of the reaction mixture. The resulting pale yellow oil was essentially pure product, slightly contaminated by starting materials, n.m.r. δ ($CCl_4$) 7.23 (5H, s), 7.06 (5H, s), 5.03 (2H, s), 3.23 (2H, s) and 2.73 (4H, s).

DESCRIPTION 1(c)

5-Benzyl diethyl 4-(2-phenylethyl)-pyrrole-2-acetate-3,5-dicarboxylate

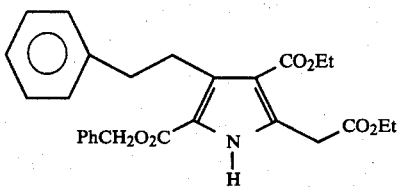

The benzyl ester (101.6 g, 0.36 mole) from Description 1(b) in glacial acetic acid (240 ml) was cooled to 5° and a solution of sodium nitrite (33 g) in water (50 ml) was added dropwise with stirring between the limited 5°–7°. The reaction mixture was then stirred at room temperature for 2 hours, stored overnight at −20° and stirred for a further 5 hours at room temperature before adding dropwise to a stirred solution of diethyl acetonedicarboxylate (94.3 ml) in glacial acetic acid (390 ml) at 70° with concurrent addition of zinc powder (102 g) mixed with sodium acetate (114 g) at a rate sufficient to maintain the temperature below 100°. On completing this addition the mixture was refluxed for 1 hour and poured into water (6 liters) with stirring. The resulting solid was dried and recrystallized* by filtration and washed with a small amount of methanol to give the required product (81.22 g, 49%) as a white solid, mp 100°–103°, δ (CDCl$_3$) 10.2 (1H, br, s), 7.3 (5H, s), 7.07 (5H, m), 5.25 (2H, s), 4.26 (2H, q, J=7 Hz), 4.15 (2H, q, J=7 Hz), 4.02 (2H, s), 3.5–2.4 (4H, symmetrical m), 1.33 (3H, t, J=7 Hz) and 1.24 (3H, t, J=7 Hz). (Found: C, 69.80; H, 6.29; N, 3.10. C$_{27}$H$_{29}$NO$_6$ requires: C, 69.96; H, 6.31; N, 3.02%).
*from toluene/60°–80° petroleum ether, collected

DESCRIPTION 1(d)

5-Benzyl diethyl 1-methyl-4-(2-phenylethyl)pyrrole-2-acetate-3,5-dicarboxylate

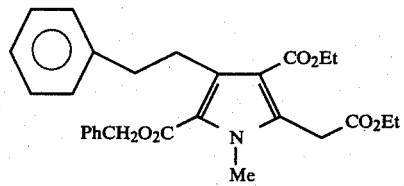

A stirred suspension of anhydrous potassium carbonate (81 g) with dimethyl sulphate (33 ml, 0.35 mole) and the N-H pyrrole from Description 1(c) (81 g, 0.175 mole) in isobutyl methyl ketone (800 ml) was refluxed overnight. A further amount of dimethyl sulphate (10 ml) and potassium carbonate (10 g) was added and the mixture refluxed for a further 5 hours before pouring into water (1,000 ml), separating the layers and washing the aqueous with ethyl acetate (3×200 ml). The combined organic layers were washed with water (2×200 ml), dried with anhydrous magnesium sulphate, filtered and the solvent evaporated. The product was purified by crystallization from toluene/60°–80° petrol to give a white solid (70.04 g, 84%), m.p. 84°–86°, δ (CDCl$_3$) 7.31 (5H, s), 7.06 (5H, m), 5.28 (2H, s), 4.25 (2H, q, J=7 Hz), 4.17 (2H, q, J=7 Hz), 4.08 (2H, s), 3.79 (3H, s), 3.6–2.4 (4H, symmetrical m). (Found: C, 70.49; H 6.57; N, 3.01. C$_{28}$H$_{31}$NO$_6$ requires: C, 70.42; H, 6.54; N, 2.93%).

DESCRIPTION 1(e)

Diethyl 4-(2-phenylethyl)pyrrole-2-acetate-3-carboxylate-5-carboxylic acid

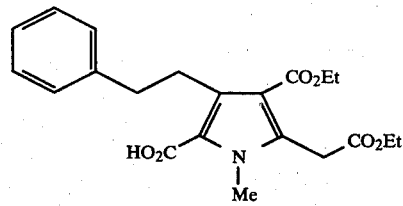

The benzyl ester from Description 1(d) (68.98 g, 0.145 mole) in ethyl acetate (1,000 ml) was hydrogenated at atmospheric pressure over 10% palladium on charcoal (3.5 g). When the theoretical amount of hydrogen had been taken up the catalyst was filtered off and the filtrate evaporated to dryness to give a white solid (53.2 g, 95%), δ (CDCl$_3$) 11.83 (1H, br., s), 7.2 (5H, br., s), 4.28 (2H, q, J=7 Hz), 4.13 (2H, q, J=7 Hz), 4.1 (2H, s), 3.83 (3H, s), 3.7–2.6 (4H, symmetrical m), 1.33 (3H, t, J=7 Hz), and 1.25 (3H, t, J=7 Hz).

DESCRIPTION 1(f)

Diethyl 4,5-dihydro-10H-1-methyl-10-oxobenzo-[5,6]cyclohepta[1,2-b]pyrrole-2-acetate-3-carboxylate

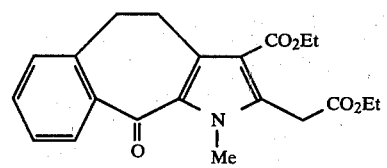

The acid from Description 1(e) (53 g, 0.137 mole) with oxalylchloride (26.1 g, 0.206 mole) in dry toluene (800 ml) was heated to reflux for 6 hours. After cooling and evaporating to dryness the resulting acid chloride was dissolved in dichloromethane (600 ml), powdered aluminum chloride (21.3 g, 0.16 mole) added in portions with stirring and then the mixture refluxed for 5½ hours. The reaction was followed by u.v. spectroscopy and by t.l.c. After leaving to stand overnight at room temperature the mixture was poured onto ice/water (500 ml), allowed to stir for 1 hour and the layers separated. The aqueous layer was extracted with dichloromethane (3×200 ml), the combined organics washed with water (2×200 ml), dried (anhydrous MgSO$_4$) and the solvent evaporated to give a red oil. N.m.r. spectroscopy of the crude product indicated that a conversion greater than 70% had been obtained. A small sample was purified by column chromatography on silica gel with 1:1 ether:6-0°–80° petroleum ether as eluant. The fractions containing the required product were recrystallized from 60°–80° petroleum ether to give a white crystalline solid, m.p. 71°–72°, δ(CDCl$_3$) 7.9–7.7 (1H, m), 7.0–7.5 (3H, m), 4.5–3.9 (4H, overlapping q, J=7 Hz), 4.14 (2H, s), 3.93 (3H, s), 3.5–2.8 (4H, m), 1.32 (3H, t, J=7 Hz) and 1.22 (3H, t, J=7 Hz).

DESCRIPTION 1 (g)

Diethyl 10H-1-methyl-10-oxobenzo[5,6]cyclohepta[1,2-b]pyrrole-2-acetate-3-carboxylate

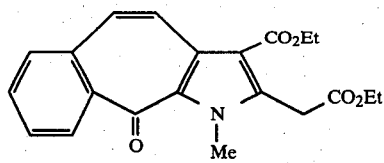

(i) A solution of the crude diester from Description 1(f) (0.57 g, 0.0015 mole) with N-bromosuccinimide (0.28 g, 0.0016 mole) and 2,2'-azobis (2-methylpropion itrile) (35 mg) in dry carbontetrachloride (10 ml) was refluxed for 1½ hours. After cooling and filtering the reaction mixture was evaporated to dryness before dissolving in ethanol (10 ml) and being treated with a solution of sodium (0.12 g) in ethanol (5 ml) and refluxed for 1½ hours. After standing at room temperature overnight the mixture was poured into water (100 ml) and extracted with chloroform (3×50 ml). The combined organic solutions were washed with water (2×50 ml), dried with anhydrous magnesium sulphate, filtered, and evaporated to dryness to give a red oil, (0.6 g). Purification by column chromatography on silica gel (20 g) eluted with ether gave the required product as a white crystalline solid, $\delta$ (CDCl$_3$) 8.65−8.35 (1H, m), 8.03 (1H, d, J=12 Hz), 7.7−7.35 (3H, m), 7.02 (1H, d, J=12 Hz), 4.5−3.8 (4H, overlapping d, J=7 Hz), 4.13 (2H, s), 3.98 (3H, s), 1.35 (3H, t, J=7 Hz) and 1.22 (3H, t, J=7 Hz).

(ii) Alternatively a solution of the diester (0.55 g, 0.0015 mole) with N-bromo succinimide (0.54 g, 0.0031 mole) and 2,2'-azobis-(2-methylpropionitrile) (70 mg) in dry carbontetrachloride (15 ml) was refluxed for 5¾ hours. A further quantity of N-bromosuccinimide (0.6 g) and 2,2'-azobis-(2-methyl-propionitrile) (70 mg) was added and the solution refluxed for a further 2 hours. After allowing to cool the solution was filtered and evaporated to dryness to give a red oil containing diethyl 4,5-dibromo-4,5-dihydro-10H-1-methyl-10-oxo-benzo[5,6]cycylohepta[1,2-b]pyrrole-2-acetate-2-carboxylate

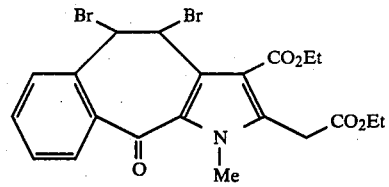

as the major component, $\delta$ (CDCl$_3$) 8.0−7.7 (1H, m), 7.6−6.8 (3H, m), 6.58 (1H, d, J=6 Hz), 5.48 (1H, d, J=6 Hz), 4.5−3.8 (4H, overlapping d, J=7 Hz), 4.07 (2H, s), 3.86 (3H, s), 1.35 (3H, t, J=7 Hz), and 1.2 (3H, t, J=7 Hz).

Zinc powder (0.3 g) was added to a solution of the crude dibromo compound in methanol (10 ml) and the mixture stirred at room temperature for 2 hours before filtering and evaporating to dryness. Purification by column chromatography on silica gel (30 g) eluted with 1:1 ether: 60°-80° petroleum ether gave the required dehydro compound with spectroscopic properties as the sample obtained in section (a).

DESCRIPTION 1(h)

10H-1-Methyl-10-oxobenzo[5,6]cyclohepta-[1,2-b]pyrrole-2-acetic acid-3-carboxylic acid

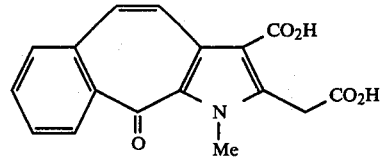

The dehydro diester from Description 1(g) (1.76 g, 0.0048 mole) was refluxed for 3 hours with 25% aqueous sodium hydroxide (30 ml). After cooling the solution was diluted with water (100 ml), washed with ether (3×50 ml), filtered and acidified with dilute hydrochloric acid to give a white precipitate of the crude diacid, $\delta$((CD$_3$)$_2$SO) 8.55−8.25 (1H, m), 8.08 (1H, d, J=12 Hz), 7.85−7.38 (3H, m), 7.15 (1H, d, J=12 Hz), 6.71 (2H, br.,s), 4.28 (2H, s) and 3.94 (3H, s).

DESCRIPTION 1(i)

Ethyl 10H-1-methyl-10-oxobenzo[5,6]cyclohepta[1,2-b]pyrrole-2-acetate-3-carboxylic acid

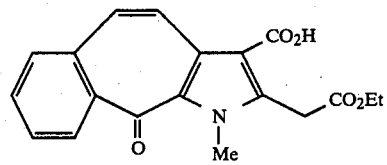

A suspension of the crude diacid from Description 1(h) (1.49 g, 0.0048 mole) in 0.5% HCl in ethanol (20 ml) was refluxed for 1¾ hours, cooled and the resulting solid collected, washed with a small volume of cold ethanol and dried to afford the desired product as pale yellow crystals (1.32 g, 81%), m.p., 221°-226°, $\delta$ (CDCl$_3$/C$_5$D$_5$N) 8.65−8.35 (1H, M), 8.35 (1H, d, J=12 Hz), 8.13 (1H, br., s), 7.6−7.3 (3H, m), 7.05 (1H, d, J=12 Hz), 4.4 (2H, s), 4.12 (2H, q, J=7 Hz), 4.03 (3H, s) and 1.2 (3H, t, J=7 Hz).

DESCRIPTION 1(j)

Ethyl 10H-1-methyl-10-oxobenzo[5,6]cyclohepta[1,2-b]pyrrole-2-acetate

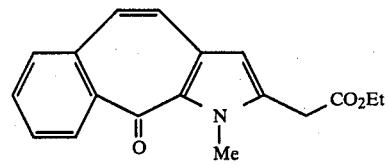

The acid (1.32 g, 0.0039 mole) from Description 1(i) was heated for 3½ hours between the limits 210°-240° under nitrogen. The resulting brown solid was washed repeatedly with ethylacetate and the combined organics washed with dilute aqueous sodium hydroxide and then with water. The organic solution was then dried (anhydrous MgSO₄) filtered and evaporated to dryness to give brown oil (0.8 g). Purification by column chromatography on silica gel (20 g) eluted with 2:1 60°–80° petroleum ether: ether gave the required product as a pale yellow solid, δ (CDCl₃) 8.85–8.5 (1H, m), 7.57–7.27 (3H, m), 6.85 (2H, s), 6.20 (1H, s), 4.07 (2H, q, J=7 Hz), 3.98 (3H, s), 3.61 (2H, s) and 1.2 (3H, t, J=7 Hz).

EXAMPLE 1

10H-1-Methyl-10-oxabenzo[5,6]cyclohepta[1,2-b]pyrrole-2-acetic acid

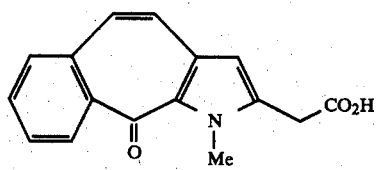

The ethyl ester (0.26 g, 0.00088 mole) from Description 1(j) was refluxed in ethanol (20 ml) and 5% aqueous hydroxide (30 ml) for 1½ hours, then poured into water (100 ml), extracted with ethyl acetate (2×100 ml) and the aqueous layer filtered before acidifying with dilute hydrochloric acid. The resulting precipitate was collected by filtration, washed with water and dried to give the crude product as a pale yellow solid (0.177 g, 75%) which was purified by recrystallization from chloroform/60°–80° petroleum ether, m.p. 150°–153°, δ (CDCl₃/CD₃OD) 8.8–8.6 (1H, m), 7.75–7.4 (3H, m), 7.15 (1H, d, J=12 Hz), 6.98 (1H, d, J=12 Hz), 6.43 (1H, s), 4.11 (3H, s) and 4.03 (2H, s).

Pharmacological Data Section

The compounds were examined for Anti-Inflammatory Activity in two conventional tests, the Cotton Pellet Granuloma test and the Carrageenin test.

The compounds were also examined for Analgesic Activity in the conventional phenyl quinone writhing test.

The results obtained are shown in the table.

No toxic effects were observed in any of these tests.

| | Dose mg/kg and (% Inhibition) *significantly active | | |
|---|---|---|---|
| | Cotton Pellet | Carrageenin | Writhing Analgesic Test |
| 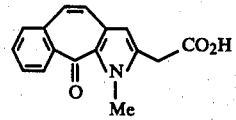 | | | 15(22)* |

What we claim is:
1. A compound of the formula:

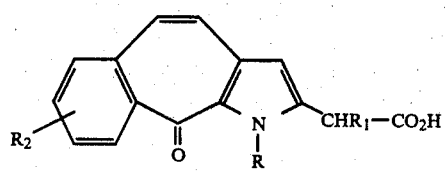

wherein
R is alkyl of 1 to 4 carbon atoms;
R₁ is hydrogen or alkyl of 1 to 4 carbon atoms;
R₂ is hydrogen, halo, alkyl of 1 to 4 carbon atoms, alkoxy of 1 to 4 carbon atoms, or alkylthio of 1 to 4 carbon atoms; and the pharmaceutically acceptable salts of said compounds.

2. A compound according to claim 1, wherein said compound is of formula:

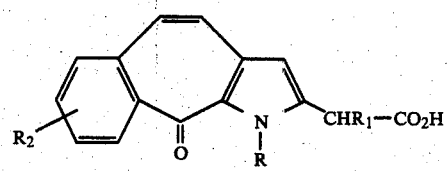

wherein
R₁ is hydrogen or methyl and
R₂ is hydrogen, chloo, chloo, bromo, methyl, ethyl, propyl, methoxy or methylthio.

3. A compound according to claim 2, wherein R₂ is in the 7- position.

4. A compound according to claim 2, wherein R₂ is hydrogen.

5. A compound according to claim 2, wherein R₁ is hydrogen.

* * * * *